US007098318B2

United States Patent
Lee et al.

(10) Patent No.: US 7,098,318 B2
(45) Date of Patent: Aug. 29, 2006

(54) FUSION PROTEIN HAVING ENHANCED IN VIVO ACTIVITY OF ERYTHROPOIETIN

(75) Inventors: Dong-Eok Lee, Seoul (KR); Myung-Suk Oh, Icheon-Shi (KR); Bo-Sup Chung, Anyang-Shi (KR); Ji-Sook Park, Seoul (KR); Ki-Wan Kim, Seoul (KR)

(73) Assignee: Cheil Jedang Corporation, (KR)

( * ) Notice: Subject to any disclaimer, the term of this patent is extended or adjusted under 35 U.S.C. 154(b) by 688 days.

(21) Appl. No.: 10/230,454

(22) Filed: Aug. 29, 2002

(65) Prior Publication Data

US 2003/0124115 A1    Jul. 3, 2003

(30) Foreign Application Priority Data

Nov. 29, 2001    (KR) ................. 2001-74975

(51) Int. Cl.
*C07K 14/59* (2006.01)
*C07H 21/00* (2006.01)
*C12P 21/06* (2006.01)
*A61K 38/24* (2006.01)

(52) U.S. Cl. .................... 530/397; 536/23.4; 435/69.1; 530/399

(58) Field of Classification Search ..................... None
See application file for complete search history.

(56) References Cited

U.S. PATENT DOCUMENTS 6,342,220 B1 *    1/2002    Adams et al. ........... 424/153.1
6,608,183 B1 *    8/2003    Cox, III ..................... 530/399

OTHER PUBLICATIONS

Wang et al., Virology 15: 5-8, 2001.*

* cited by examiner

*Primary Examiner*—Eileen B. O'Hara
*Assistant Examiner*—Gyan Chandra
(74) *Attorney, Agent, or Firm*—Peter F. Corless; Christine C. O'Day; Edwards Angell Palmer & Dodge LLP

(57) ABSTRACT

The present invention relates to a fusion protein having enhanced in vivo activity of erythropoietin wherein a carboxy terminal peptide fragment of thrombopoietin is fused with the carboxy terminal of human erythropoietin. This fusion protein has highly enhanced in vivo half-life due to increased carbohydrate content without loss of the inherent activity of erythropoietin, and does not cause any antigenicity when applied to the human body.

3 Claims, 8 Drawing Sheets

FIGURE 1a

Nucleotide and Amino Acid Sequences of Carboxy Terminal of TPO(LTP)

```
                                        GCC CCA CCC ACC ACA GCT GTC CCC
                                        Ala Pro Pro Thr Thr Ala Val Pro

AGC AGA ACC TCT CTA GTC CTC ACA CTG AAC GAG CTC CCA AAC AGG ACT TCT GGA TTG TTG
Ser Arg Thr Ser Leu Val Leu Thr Leu Asn Glu Leu Pro Asn Arg Thr Ser Gly Leu Leu

GAG ACA AAC TTC ACT GCC TCA GCC AGA ACT ACT GGC TCT GGG CTT CTG AAG TGG CAG CAG
Glu Thr Asn Phe Thr Ala Ser Ala Arg Thr Thr Gly Ser Gly Leu Leu Lys Trp Gln Gln

GGA TTC AGA GCC AAG ATT CCT GGT CTG CTG AAC CAA ACC TCC AGG TCC CTG GAC CAA ATC
Gly Phe Arg Ala Lys Ile Pro Gly Leu Leu Asn Gln Thr Ser Arg Ser Leu Asp Gln Ile

CCC GGA TAC CTG AAC AGG ATA CAC GAA CTC TTG AAT GGA ACT CGT GGA CTC TTT CCT GGA
Pro Gly Tyr Leu Asn Arg Ile His Glu Leu Leu Asn Gly Thr Arg Gly Leu Phe Pro Gly

CCC TCA CGC AGG ACC CTA GGA GCC CCG GAC ATT TCC TCA GGA ACA TCA GAC ACA GGC TCC
Pro Ser Arg Arg Thr Leu Gly Ala Pro Asp Ile Ser Ser Gly Thr Ser Asp Thr Gly Ser

CTG CCA CCC AAC CTC CAG CCT GGA TAT TCT CCT TCC CCA ACC CAT CCT CCT ACT GGA CAG
Leu Pro Pro Asn Leu Gln Pro Gly Tyr Ser Pro Ser Pro Thr His Pro Pro Thr Gly Gln

TAT ACG CTC TTC CCT CTT CCA CCC ACC TTG CCC ACC CCT GTG GTC CAG CTC CAC CCC CTG
Tyr Thr Leu Phe Pro Leu Pro Pro Thr Leu Pro Thr Pro Val Val Gln Leu His Pro Leu

CTT CCT GAC CCT TCT GCT CCA ACG CCC ACC CCT ACC AGC CCT CTT CTA AAC ACA TCC TAC
Leu Pro Asp Pro Ser Ala Pro Thr Pro Thr Pro Thr Ser Pro Leu Leu Asn Thr Ser Tyr

ACC CAC TCC CAG AAT CTG TCT CAG GAA GGG TAA
Thr His Ser Gln Asn Leu Ser Gln Glu Gly ter
```

FIGURE 1b

Nucleotide and Amino Acid Sequences of Carboxy Terminal of TPO(STP)

CCT CTT CTA AAC ACA TCC TAC ACC CAC TCC CAG AAT CTG TCT CAG GAA GGG TAA
Pro Leu Leu Asn Thr Ser Tyr Thr His Ser Gln Asn Leu Ser Gln Glu Gly ter

FIGURE 2aa

Nucleotide and Amino Acid Sequences of ELTP

```
1                5                10               15               20
ATG GGG GTG CAC GAA TGT CCT GCC TGG CTG TGG CTT CTC CTG TCC CTG CTG TCG CTC CCT
Met Gly Val His Glu Cys Pro Ala Trp Leu Trp Leu Leu Leu Ser Leu Leu Ser Leu Pro

CTG GGC CTC CCA GTC CTG GGC GCC CCA CCA CGC CTC ATC TGT GAC AGC CGA GTC CTG GAG
Leu Gly Leu Pro Val Leu Gly Ala Pro Pro Arg Leu Ile Cys Asp Ser Arg Val Leu Glu

AGG TAC CTC TTG GAG GCC AAG GAG GCC GAG AAT ATC ACG ACG GGC TGT GCT GAA CAC TGC
Arg Tyr Leu Leu Glu Ala Lys Glu Ala Glu Asn Ile Thr Thr Gly Cys Ala Glu His Cys

AGC TTG AAT GAG AAT ATC ACT GTC CCA GAC ACC AAA GTT AAT TTC TAT GCC TGG AAG AGG
Ser Leu Asn Glu Asn Ile Thr Val Pro Asp Thr Lys Val Asn Phe Tyr Ala Trp Lys Arg

ATG GAG GTC GGG CAG CAG GCC GTA GAA GTC TGG CAG GGC CTG GCC CTG CTG TCG GAA GCT
Met Glu Val Gly Gln Gln Ala Val Glu Val Trp Gln Gly Leu Ala Leu Leu Ser Glu Ala

GTC CTG CGG GGC CAG GCC CTG TTG GTC AAC TCT TCC CAG CCG TGG GAG CCC CTG CAG CTG
Val Leu Arg Gly Gln Ala Leu Leu Val Asn Ser Ser Gln Pro Trp Glu Pro Leu Gln Leu

CAT GTG GAT AAA GCC GTC AGT GGC CTT CGC AGC CTC ACC ACT CTG CTT CGG GCT CTG GGA
His Val Asp Lys Ala Val Ser Gly Leu Arg Ser Leu Thr Thr Leu Leu Arg Ala Leu Gly

GCC CAG AAG GAA GCC ATC TCC CCT CCA GAT GCG GCC TCA GCT GCT CCA CTC CGA ACA ATC
Ala Gln Lys Glu Ala Ile Ser Pro Pro Asp Ala Ala Ser Ala Ala Pro Leu Arg Thr Ile

ACT GCT GAC ACT TTC CGC AAA CTC TTC CGA GTC TAC TCC AAT TTC CTC CGG GGA AAG CTG
Thr Ala Asp Thr Phe Arg Lys Leu Phe Arg Val Tyr Ser Asn Phe Leu Arg Gly Lys Leu

AAG CTG TAC ACA GGG GAG GCC TGC AGG ACA GGG GAC GCC CCA CCC ACC ACA GCT GTC CCC
Lys Leu Tyr Thr Gly Glu Ala Cys Arg Thr Gly Asp Ala Pro Pro Thr Thr Ala Val Pro

AGC AGA ACC TCT CTA GTC CTC ACA CTG AAC GAG CTC CCA AAC AGG ACT TCT GGA TTG TTG
Ser Arg Thr Ser Leu Val Leu Thr Leu Asn Glu Leu Pro Asn Arg Thr Ser Gly Leu Leu

GAG ACA AAC TTC ACT GCC TCA GCC AGA ACT ACT GGC TCT GGG CTT CTG AAG TGG CAG CAG
Glu Thr Asn Phe Thr Ala Ser Ala Arg Thr Thr Gly Ser Gly Leu Leu Lys Trp Gln Gln

GGA TTC AGA GCC AAG ATT CCT GGT CTG CTG AAC CAA ACC TCC AGG TCC CTG GAC CAA ATC
Gly Phe Arg Ala Lys Ile Pro Gly Leu Leu Asn Gln Thr Ser Arg Ser Leu Asp Gln Ile

CCC GGA TAC CTG AAC AGG ATA CAC GAA CTC TTG AAT GGA ACT CGT GGA CTC TTT CCT GGA
Pro Gly Tyr Leu Asn Arg Ile His Glu Leu Leu Asn Gly Thr Arg Gly Leu Phe Pro Gly

CCC TCA CGC AGG ACC CTA GGA GCC CCG GAC ATT TCC TCA GGA ACA TCA GAC ACA GGC TCC
Pro Ser Arg Arg Thr Leu Gly Ala Pro Asp Ile Ser Ser Gly Thr Ser Asp Thr Gly Ser

CTG CCA CCC AAC CTC CAG CCT GGA TAT TCT CCT TCC CCA ACC CAT CCT CCT ACT GGA CAG
```

FIGURE 2ab

```
Leu Pro Pro Asn Leu Gln Pro Gly Tyr Ser Pro Ser Pro Thr His Pro Pro Thr Gly Gln

TAT ACG CTC TTC CCT CTT CCA CCC ACC TTG CCC ACC CCT GTG GTC CAG CTC CAC CCC CTG
Tyr Thr Leu Phe Pro Leu Pro Pro Thr Leu Pro Thr Pro Val Val Gln Leu His Pro Leu

CTT CCT GAC CCT TCT GCT CCA ACG CCC ACC CCT ACC AGC CCT CTT CTA AAC ACA TCC TAC
Leu Pro Asp Pro Ser Ala Pro Thr Pro Thr Pro Thr Ser Pro Leu Leu Asn Thr Ser Tyr

ACC CAC TCC CAG AAT CTG TCT CAG GAA GGG TAA
Thr His Ser Gln Asn Leu Ser Gln Glu Gly ter
```

FIGURE 2b

Nucleotide and Amino Acid Sequences of ESTP

```
1               5                   10                  15                  20
ATG GGG GTG CAC GAA TGT CCT GCC TGG CTG TGG CTT CTC CTG TCC CTG CTG TCG CTC CCT
Met Gly Val His Glu Cys Pro Ala Trp Leu Trp Leu Leu Leu Ser Leu Leu Ser Leu Pro

CTG GGC CTC CCA GTC CTG GGC GCC CCA CCA CGC CTC ATC TGT GAC AGC CGA GTC CTG GAG
Leu Gly Leu Pro Val Leu Gly Ala Pro Pro Arg Leu Ile Cys Asp Ser Arg Val Leu Glu

AGG TAC CTC TTG GAG GCC AAG GAG GCC GAG AAT ATC ACG ACG GGC TGT GCT GAA CAC TGC
Arg Tyr Leu Leu Glu Ala Lys Glu Ala Glu Asn Ile Thr Thr Gly Cys Ala Glu His Cys

AGC TTG AAT GAG AAT ATC ACT GTC CCA GAC ACC AAA GTT AAT TTC TAT GCC TGG AAG AGG
Ser Leu Asn Glu Asn Ile Thr Val Pro Asp Thr Lys Val Asn Phe Tyr Ala Trp Lys Arg

ATG GAG GTC GGG CAG CAG GCC GTA GAA GTC TGG CAG GGC CTG GCC CTG CTG TCG GAA GCT
Met Glu Val Gly Gln Gln Ala Val Glu Val Trp Gln Gly Leu Ala Leu Leu Ser Glu Ala

GTC CTG CGG GGC CAG GCC CTG TTG GTC AAC TCT TCC CAG CCG TGG GAG CCC CTG CAG CTG
Val Leu Arg Gly Gln Ala Leu Leu Val Asn Ser Ser Gln Pro Trp Glu Pro Leu Gln Leu

CAT GTG GAT AAA GCC GTC AGT GGC CTT CGC AGC CTC ACC ACT CTG CTT CGG GCT CTG GGA
His Val Asp Lys Ala Val Ser Gly Leu Arg Ser Leu Thr Thr Leu Leu Arg Ala Leu Gly

GCC CAG AAG GAA GCC ATC TCC CCT CCA GAT GCG GCC TCA GCT GCT CCA CTC CGA ACA ATC
Ala Gln Lys Glu Ala Ile Ser Pro Pro Asp Ala Ala Ser Ala Ala Pro Leu Arg Thr Ile

ACT GCT GAC ACT TTC CGC AAA CTC TTC CGA GTC TAC TCC AAT TTC CTC CGG GGA AAG CTG
Thr Ala Asp Thr Phe Arg Lys Leu Phe Arg Val Tyr Ser Asn Phe Leu Arg Gly Lys Leu

AAG CTG TAC ACA GGG GAG GCC TGC AGG ACA GGG GAC CCT CTT CTA AAC ACA TCC TAC ACC
Lys Leu Tyr Thr Gly Glu Ala Cys Arg Thr Gly Asp Pro Leu Leu Asn Thr Ser Tyr Thr

CAC TCC CAG AAT CTG TCT CAG GAA GGG TAA
His Ser Gln Asn Leu Ser Gln Glu Gly ter
```

Construction Scheme of Expression Vecter pcDNA-ESTP

SEQUENCE LISTING

<160> NUMBER OF SEQ ID NOS: 18

<210> SEQ ID NO 1
<211> LENGTH: 178
<212> TYPE: PRT
<213> ORGANISM: Homo sapiens
<220> FEATURE:
<221> NAME/KEY: PEPTIDE
<222> LOCATION: (1)..(178)
<223> OTHER INFORMATION: Amino acids in the positions of 176 to 353 of
      human thrombopoietin (TPO)

<400> SEQUENCE: 1

Ala Pro Pro Thr Thr Ala Val Pro Ser Arg Thr Ser Leu Val Leu Thr
 1               5                  10                  15

Leu Asn Glu Leu Pro Asn Arg Thr Ser Gly Leu Leu Glu Thr Asn Phe
            20                  25                  30

Thr Ala Ser Ala Arg Thr Thr Gly Ser Gly Leu Leu Lys Trp Gln Gln
         35                  40                  45

Gly Phe Arg Ala Lys Ile Pro Gly Leu Leu Asn Gln Thr Ser Arg Ser
 50                  55                  60

Leu Asp Gln Ile Pro Gly Tyr Leu Asn Arg Ile His Glu Leu Leu Asn
 65                  70                  75                  80

Gly Thr Arg Gly Leu Phe Pro Gly Pro Ser Arg Arg Thr Leu Gly Ala
                 85                  90                  95

Pro Asp Ile Ser Ser Gly Thr Ser Asp Thr Gly Ser Leu Pro Pro Asn
            100                 105                 110

Leu Gln Pro Gly Tyr Ser Pro Ser Pro Thr His Pro Pro Thr Gly Gln
            115                 120                 125

Tyr Thr Leu Phe Pro Leu Pro Pro Thr Leu Pro Thr Pro Val Val Gln
130                 135                 140

Leu His Pro Leu Leu Pro Asp Pro Ser Ala Pro Thr Pro Thr Pro Thr
145                 150                 155                 160

Ser Pro Leu Leu Asn Thr Ser Tyr Thr His Ser Gln Asn Leu Ser Gln
                165                 170                 175

Glu Gly

<210> SEQ ID NO 2
<211> LENGTH: 17
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: Amino acids in the positions of 337 to 353 of
      human thrombopoietin (TPO)

<400> SEQUENCE: 2

Pro Leu Leu Asn Thr Ser Tyr Thr His Ser Gln Asn Leu Ser Gln Glu
 1               5                  10                  15

Gly

<210> SEQ ID NO 3
<211> LENGTH: 370
<212> TYPE: PRT
<213> ORGANISM: Artificial Sequence
<220> FEATURE:
<223> OTHER INFORMATION: Description of Artificial Sequence: Fusion
      protein (ELTP) of erythropoietin (EPO) and carboxy terminal
      peptide (LTP) of human thrombopoietin

<400> SEQUENCE: 3

```
Met Gly Val His Glu Cys Pro Ala Trp Leu Trp Leu Leu Leu Ser Leu
 1               5                  10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
 65                 70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Ala Pro Pro Thr Thr Ala Val Pro Ser Arg Thr Ser Leu Val Leu Thr
                195                 200                 205

Leu Asn Glu Leu Pro Asn Arg Thr Ser Gly Leu Leu Glu Thr Asn Phe
                210                 215                 220

Thr Ala Ser Ala Arg Thr Thr Gly Ser Gly Leu Leu Lys Trp Gln Gln
225                 230                 235                 240

Gly Phe Arg Ala Lys Ile Pro Gly Leu Leu Asn Gln Thr Ser Arg Ser
                245                 250                 255

Leu Asp Gln Ile Pro Gly Tyr Leu Asn Arg Ile His Glu Leu Leu Asn
                260                 265                 270

Gly Thr Arg Gly Leu Phe Pro Gly Pro Ser Arg Arg Thr Leu Gly Ala
                275                 280                 285

Pro Asp Ile Ser Ser Gly Thr Ser Asp Thr Gly Ser Leu Pro Pro Asn
                290                 295                 300

Leu Gln Pro Gly Tyr Ser Pro Ser Pro Thr His Pro Pro Thr Gly Gln
305                 310                 315                 320

Tyr Thr Leu Phe Pro Leu Pro Pro Thr Leu Pro Thr Pro Val Val Gln
                325                 330                 335

Leu His Pro Leu Leu Pro Asp Pro Ser Ala Pro Thr Pro Thr Pro Thr
                340                 345                 350

Ser Pro Leu Leu Asn Thr Ser Tyr Thr His Ser Gln Asn Leu Ser Gln
                355                 360                 365

Glu Gly
    370
```

<210> SEQ ID NO 4
<211> LENGTH: 209
<212> TYPE: PRT

<213> ORGANISM: Artificial Sequence
<220> FEATURE:
<223> OTHER INFORMATION: Description of Artificial Sequence: Fusion
      protein (ESTP) of erythropoietin (EPO) and carboxy terminal
      peptide (STP) of human thrombopoietin

<400> SEQUENCE: 4

Met Gly Val His Glu Cys Pro Ala Trp Leu Trp Leu Leu Ser Leu
 1               5                  10                  15

Leu Ser Leu Pro Leu Gly Leu Pro Val Leu Gly Ala Pro Pro Arg Leu
             20                  25                  30

Ile Cys Asp Ser Arg Val Leu Glu Arg Tyr Leu Leu Glu Ala Lys Glu
         35                  40                  45

Ala Glu Asn Ile Thr Thr Gly Cys Ala Glu His Cys Ser Leu Asn Glu
     50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Pro Leu Leu Asn Thr Ser Tyr Thr His Ser Gln Asn Leu Ser Gln Glu
        195                 200                 205

Gly

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Primer EP1
      having the nucleotide sequence complementary to the terminal
      sequence of EPO cDNA

<400> SEQUENCE: 5
atgggggcac gaatgtcctg cctggctgg                                    29

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer EP2
      having the nucleotide sequence complementary to the terminal
      sequence of EPO cDNA

<400> SEQUENCE: 6
gtcccctgtc ctgcaggcct                                              20

<210> SEQ ID NO 7

```
<211> LENGTH: 24
<212> TYPE: DNA
<213> ORGANISM: Artificial Sequence
<220> FEATURE:
<223> OTHER INFORMATION: Description of Artificial Sequence: Primer T1
      having the nucleotide sequence complementary to the terminal
      sequene of TPO cDNA

<400> SEQUENCE: 7
atggatctga ctgaattgct cctc                                          24

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Primer T2
      having the nucleotide sequence complementary to the terminal
      sequecne of TPO cDNA

<400> SEQUENCE: 8
ttacccttcc tgagacagat tctggga                                       27

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Primer EL1
      for PCR to obtain the desired gene LTP

<400> SEQUENCE: 9
gaggcctgca ggacagggga cgccccaccc accacagctg tcc                     43

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Primer
      EP11 for PCR to obtain the desired fusion gene ELTP and ESTP

<400> SEQUENCE: 10
taagcttatg ggggtgcacg aatgt                                         25

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Primer L2
      for PCR to obtain the desired fusion gene ELTP and ESTP

<400> SEQUENCE: 11
tggattctta cccttcctga gacagattc                                     29

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Primer ES1
      for PCR shuffling to obtain the desired gene STP

<400> SEQUENCE: 12
aggggaggcc tgcaggacag gggaccctct tctaa                              35
```

```
<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Primer S2
      for PCR shuffling to obtain the desired gene STP

<400> SEQUENCE: 13
gtgggtgtag gatgtgttta gaagagg                                          27

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Primer S3
      for PCR shuffling to obtian the desired gene STP

<400> SEQUENCE: 14
tacacccact cccagaatct gtctc                                            25

<210> SEQ ID NO 15
<211> LENGTH: 537
<212> TYPE: DNA
<213> ORGANISM: Homo sapiens
<220> FEATURE:
<221> NAME/KEY: CDS
<222> LOCATION: (1)..(534)

<400> SEQUENCE: 15
```

| | | | | | | | | | | | | | | | | |
|---|---|---|---|---|---|---|---|---|---|---|---|---|---|---|---|---|
| gcc | cca | ccc | acc | aca | gct | gtc | ccc | agc | aga | acc | tct | cta | gtc | ctc | aca | 48 |
| Ala | Pro | Pro | Thr | Thr | Ala | Val | Pro | Ser | Arg | Thr | Ser | Leu | Val | Leu | Thr | |
| 1 | | | | 5 | | | | | 10 | | | | | 15 | | |
| ctg | aac | gag | ctc | cca | aac | agg | act | tct | gga | ttg | ttg | gag | aca | aac | ttc | 96 |
| Leu | Asn | Glu | Leu | Pro | Asn | Arg | Thr | Ser | Gly | Leu | Leu | Glu | Thr | Asn | Phe | |
| | | | | 20 | | | | | 25 | | | | | 30 | | |
| act | gcc | tca | gcc | aga | act | act | ggc | tct | ggg | ctt | ctg | aag | tgg | cag | cag | 144 |
| Thr | Ala | Ser | Ala | Arg | Thr | Thr | Gly | Ser | Gly | Leu | Leu | Lys | Trp | Gln | Gln | |
| | | 35 | | | | | 40 | | | | | 45 | | | | |
| gga | ttc | aga | gcc | aag | att | cct | ggt | ctg | ctg | aac | caa | acc | tcc | agg | tcc | 192 |
| Gly | Phe | Arg | Ala | Lys | Ile | Pro | Gly | Leu | Leu | Asn | Gln | Thr | Ser | Arg | Ser | |
| | 50 | | | | | 55 | | | | | 60 | | | | | |
| ctg | gac | caa | atc | ccc | gga | tac | ctg | aac | agg | ata | cac | gaa | ctc | ttg | aat | 240 |
| Leu | Asp | Gln | Ile | Pro | Gly | Tyr | Leu | Asn | Arg | Ile | His | Glu | Leu | Leu | Asn | |
| 65 | | | | | 70 | | | | | 75 | | | | | 80 | |
| gga | act | cgt | gga | ctc | ttt | cct | gga | ccc | tca | cgc | agg | acc | cta | gga | gcc | 288 |
| Gly | Thr | Arg | Gly | Leu | Phe | Pro | Gly | Pro | Ser | Arg | Arg | Thr | Leu | Gly | Ala | |
| | | | | 85 | | | | | 90 | | | | | 95 | | |
| ccg | gac | att | tcc | tca | gga | aca | tca | gac | aca | ggc | tcc | ctg | cca | ccc | aac | 336 |
| Pro | Asp | Ile | Ser | Ser | Gly | Thr | Ser | Asp | Thr | Gly | Ser | Leu | Pro | Pro | Asn | |
| | | | | 100 | | | | | 105 | | | | | 110 | | |
| ctc | cag | cct | gga | tat | tct | cct | tcc | cca | acc | cat | cct | cct | act | gga | cag | 384 |
| Leu | Gln | Pro | Gly | Tyr | Ser | Pro | Ser | Pro | Thr | His | Pro | Pro | Thr | Gly | Gln | |
| | | | 115 | | | | | 120 | | | | | 125 | | | |
| tat | acg | ctc | ttc | cct | ctt | cca | ccc | acc | ttg | ccc | acc | cct | gtg | gtc | cag | 432 |
| Tyr | Thr | Leu | Phe | Pro | Leu | Pro | Pro | Thr | Leu | Pro | Thr | Pro | Val | Val | Gln | |
| | | 130 | | | | | 135 | | | | | 140 | | | | |
| ctc | cac | ccc | ctg | ctt | cct | gac | cct | tct | gct | cca | acg | ccc | acc | cct | acc | 480 |
| Leu | His | Pro | Leu | Leu | Pro | Asp | Pro | Ser | Ala | Pro | Thr | Pro | Thr | Pro | Thr | |
| 145 | | | | | 150 | | | | | 155 | | | | | 160 | |
| agc | cct | ctt | cta | aac | aca | tcc | tac | acc | cac | tcc | cag | aat | ctg | tct | cag | 528 |
| Ser | Pro | Leu | Leu | Asn | Thr | Ser | Tyr | Thr | His | Ser | Gln | Asn | Leu | Ser | Gln | |
| | | | | 165 | | | | | 170 | | | | | 175 | | | gaa ggg taa                                                                 537
Glu Gly <210> SEQ ID NO 16
<211> LENGTH: 54
<212> TYPE: DNA
<213> ORGANISM: Homo sapiens
<220> FEATURE:
<221> NAME/KEY: CDS
<222> LOCATION: (1)..(51)

<400> SEQUENCE: 16 cct ctt cta aac aca tcc tac acc cac tcc cag aat ctg tct cag gaa      48
Pro Leu Leu Asn Thr Ser Tyr Thr His Ser Gln Asn Leu Ser Gln Glu
 1               5                  10                  15 ggg taa                                                              54
Gly

<210> SEQ ID NO 17
<211> LENGTH: 1113
<212> TYPE: DNA
<213> ORGANISM: Artificial Sequence
<220> FEATURE:
<223> OTHER INFORMATION: Description of Artificial Sequence: Fusion DNA
      (ELTP) of erythropoietin (EPO)
<220> FEATURE:
<221> NAME/KEY: CDS
<222> LOCATION: (1)..(1110)

<400> SEQUENCE: 17 atg ggg gtg cac gaa tgt cct gcc tgg ctg tgg ctt ctc ctg tcc ctg      48
Met Gly Val His Glu Cys Pro Ala Trp Leu Trp Leu Leu Leu Ser Leu
 1               5                  10                  15 ctg tcg ctc cct ctg ggc ctc cca gtc ctg ggc gcc cca cca cgc ctc      96
Leu Ser Leu Pro Leu Gly Leu Pro Val Leu Gly Ala Pro Pro Arg Leu
                20                  25                  30 atc tgt gac agc cga gtc ctg gag agg tac ctc ttg gag gcc aag gag     144
Ile Cys Asp Ser Arg Val Leu Glu Arg Tyr Leu Leu Glu Ala Lys Glu
            35                  40                  45 gcc gag aat atc acg acg ggc tgt gct gaa cac tgc agc ttg aat gag     192
Ala Glu Asn Ile Thr Thr Gly Cys Ala Glu His Cys Ser Leu Asn Glu
        50                  55                  60 aat atc act gtc cca gac acc aaa gtt aat ttc tat gcc tgg aag agg     240
Asn Ile Thr Val Pro Asp Thr Lys Val Asn Phe Tyr Ala Trp Lys Arg
 65                  70                  75                  80 atg gag gtc ggg cag cag gcc gta gaa gtc tgg cag ggc ctg gcc ctg     288
Met Glu Val Gly Gln Gln Ala Val Glu Val Trp Gln Gly Leu Ala Leu
                 85                  90                  95 ctg tcg gaa gct gtc ctg cgg ggc cag gcc ctg ttg gtc aac tct tcc     336
Leu Ser Glu Ala Val Leu Arg Gly Gln Ala Leu Leu Val Asn Ser Ser
                100                 105                 110 cag ccg tgg gag ccc ctg cag ctg cat gtg gat aaa gcc gtc agt ggc     384
Gln Pro Trp Glu Pro Leu Gln Leu His Val Asp Lys Ala Val Ser Gly
            115                 120                 125 ctt cgc agc ctc acc act ctg ctt cgg gct ctg gga gcc cag aag gaa     432
Leu Arg Ser Leu Thr Thr Leu Leu Arg Ala Leu Gly Ala Gln Lys Glu
        130                 135                 140 gcc atc tcc cct cca gat gcg gcc tca gct gct cca ctc cga aca atc     480
Ala Ile Ser Pro Pro Asp Ala Ala Ser Ala Ala Pro Leu Arg Thr Ile
145                 150                 155                 160 act gct gac act ttc cgc aaa ctc ttc cga gtc tac tcc aat ttc ctc     528
Thr Ala Asp Thr Phe Arg Lys Leu Phe Arg Val Tyr Ser Asn Phe Leu
                165                 170                 175

-continued

```
cgg gga aag ctg aag ctg tac aca ggg gag gcc tgc agg aca ggg gac      576
Arg Gly Lys Leu Lys Leu Tyr Thr Gly Glu Ala Cys Arg Thr Gly Asp
            180                 185                 190 gcc cca ccc acc aca gct gtc ccc agc aga acc tct cta gtc ctc aca      624
Ala Pro Pro Thr Thr Ala Val Pro Ser Arg Thr Ser Leu Val Leu Thr
        195                 200                 205 ctg aac gag ctc cca aac agg act tct gga ttg ttg gag aca aac ttc      672
Leu Asn Glu Leu Pro Asn Arg Thr Ser Gly Leu Leu Glu Thr Asn Phe
    210                 215                 220 act gcc tca gcc aga act act ggc tct ggg ctt ctg aag tgg cag cag      720
Thr Ala Ser Ala Arg Thr Thr Gly Ser Gly Leu Leu Lys Trp Gln Gln
225                 230                 235                 240 gga ttc aga gcc aag att cct ggt ctg ctg aac caa acc tcc agg tcc      768
Gly Phe Arg Ala Lys Ile Pro Gly Leu Leu Asn Gln Thr Ser Arg Ser
                245                 250                 255 ctg gac caa atc ccc gga tac ctg aac agg ata cac gaa ctc ttg aat      816
Leu Asp Gln Ile Pro Gly Tyr Leu Asn Arg Ile His Glu Leu Leu Asn
            260                 265                 270 gga act cgt gga ctc ttt cct gga ccc tca cgc agg acc cta gga gcc      864
Gly Thr Arg Gly Leu Phe Pro Gly Pro Ser Arg Arg Thr Leu Gly Ala
        275                 280                 285 ccg gac att tcc tca gga aca tca gac aca ggc tcc ctg cca ccc aac      912
Pro Asp Ile Ser Ser Gly Thr Ser Asp Thr Gly Ser Leu Pro Pro Asn
    290                 295                 300 ctc cag cct gga tat tct cct tcc cca acc cat cct cct act gga cag      960
Leu Gln Pro Gly Tyr Ser Pro Ser Pro Thr His Pro Pro Thr Gly Gln
305                 310                 315                 320 tat acg ctc ttc cct ctt cca ccc acc ttg ccc acc cct gtg gtc cag     1008
Tyr Thr Leu Phe Pro Leu Pro Pro Thr Leu Pro Thr Pro Val Val Gln
                325                 330                 335 ctc cac ccc ctg ctt cct gac cct tct gct cca acg ccc acc cct acc     1056
Leu His Pro Leu Leu Pro Asp Pro Ser Ala Pro Thr Pro Thr Pro Thr
            340                 345                 350 agc cct ctt cta aac aca tcc tac acc cac tcc cag aat ctg tct cag     1104
Ser Pro Leu Leu Asn Thr Ser Tyr Thr His Ser Gln Asn Leu Ser Gln
        355                 360                 365 gaa ggg taa                                                         1113
Glu Gly
    370

<210> SEQ ID NO 18
<211> LENGTH: 630
<212> TYPE: DNA
<213> ORGANISM: Artificial Sequence
<220> FEATURE:
<223> OTHER INFORMATION: Description of Artificial Sequence: Fusion
      DNA of (ESTP) of erythropoietin (EPO)
<220> FEATURE:
<221> NAME/KEY: CDS
<222> LOCATION: (1)..(627)

<400> SEQUENCE: 18 atg ggg gtg cac gaa tgt cct gcc tgg ctg tgg ctt ctc ctg tcc ctg       48
Met Gly Val His Glu Cys Pro Ala Trp Leu Trp Leu Leu Leu Ser Leu
1               5                  10                  15 ctg tcg ctc cct ctg ggc ctc cca gtc ctg ggc gcc cca cca cgc ctc       96
Leu Ser Leu Pro Leu Gly Leu Pro Val Leu Gly Ala Pro Pro Arg Leu
            20                  25                  30 atc tgt gac agc cga gtc ctg gag agg tac ctc ttg gag gcc aag gag      144
Ile Cys Asp Ser Arg Val Leu Glu Arg Tyr Leu Leu Glu Ala Lys Glu
        35                  40                  45
```

-continued

```
gcc gag aat atc acg acg ggc tgt gct gaa cac tgc agc ttg aat gag      192
Ala Glu Asn Ile Thr Thr Gly Cys Ala Glu His Cys Ser Leu Asn Glu
    50                  55                  60 aat atc act gtc cca gac acc aaa gtt aat ttc tat gcc tgg aag agg      240
Asn Ile Thr Val Pro Asp Thr Lys Val Asn Phe Tyr Ala Trp Lys Arg
65                  70                  75                  80 atg gag gtc ggg cag cag gcc gta gaa gtc tgg cag ggc ctg gcc ctg      288
Met Glu Val Gly Gln Gln Ala Val Glu Val Trp Gln Gly Leu Ala Leu
                85                  90                  95 ctg tcg gaa gct gtc ctg cgg ggc cag gcc ctg ttg gtc aac tct tcc      336
Leu Ser Glu Ala Val Leu Arg Gly Gln Ala Leu Leu Val Asn Ser Ser
            100                 105                 110 cag ccg tgg gag ccc ctg cag ctg cat gtg gat aaa gcc gtc agt ggc      384
Gln Pro Trp Glu Pro Leu Gln Leu His Val Asp Lys Ala Val Ser Gly
        115                 120                 125 ctt cgc agc ctc acc act ctg ctt cgg gct ctg gga gcc cag aag gaa      432
Leu Arg Ser Leu Thr Thr Leu Leu Arg Ala Leu Gly Ala Gln Lys Glu
    130                 135                 140 gcc atc tcc cct cca gat gcg gcc tca gct gct cca ctc cga aca atc      480
Ala Ile Ser Pro Pro Asp Ala Ala Ser Ala Ala Pro Leu Arg Thr Ile
145                 150                 155                 160 act gct gac act ttc cgc aaa ctc ttc cga gtc tac tcc aat ttc ctc      528
Thr Ala Asp Thr Phe Arg Lys Leu Phe Arg Val Tyr Ser Asn Phe Leu
                165                 170                 175 cgg gga aag ctg aag ctg tac aca ggg gag gcc tgc agg aca ggg gac      576
Arg Gly Lys Leu Lys Leu Tyr Thr Gly Glu Ala Cys Arg Thr Gly Asp
            180                 185                 190 cct ctt cta aac aca tcc tac acc cac tcc cag aat ctg tct cag gaa      624
Pro Leu Leu Asn Thr Ser Tyr Thr His Ser Gln Asn Leu Ser Gln Glu
        195                 200                 205 ggg taa                                                              630
Gly
```

FUSION PROTEIN HAVING ENHANCED IN VIVO ACTIVITY OF ERYTHROPOIETIN

This application claims the prior benefit of Korean Patent Application No. 2001-74975, filed on Nov. 29, 2001.

TECHNICAL FIELD

The present invention relates to a fusion protein having enhanced in vivo activity of erythropoietin (EPO, below) that is a new medicine for the treatment of anemia. Specifically, the present invention relates to a fusion protein having highly enhanced in vivo half-life and activity of erythropoietin by fusion of EPO molecule with a certain peptide that has half-life elongation activity and is derived from the human body.

BACKGROUND ART

EPO, a glycoprotein having the molecular weight of 30,000 to 34,000, is a factor that stimulates production and differentiation of red blood cells. This protein acts by binding to receptors on erythrocyte precursor cells to result in increase of calcium ion concentration in a cell, increase of DNA biosynthesis, and stimulation for the formation of hemoglobin and the like. This EPO can be used for the treatment of anemia from renal failure, anemia of a premature baby, anemia from hypothyroidism, anemia from malnutrition, etc. The clinical use of recombinant human EPO is on the increase. However, such use may cause some inconvenience and high costs because it should be administered on the average three times a week due to its short half-life. Thus, if the in vivo activity of EPO is maintained for a long time, the administration frequency of EPO may be greatly decreased.

Efficacy of EPO is proportional to in vivo half-life thereof. It is known that in vivo half-life of EPO is correlated to the content of sialic acid that is located at the terminal of carbohydrate chains of EPO. Therefore, efficacy of EPO is highly dependent on the presence of carbohydrate chains. Since the forms of carbohydrates appear differently depending on the kind of cells where EPO is expressed, the same glycoproteins may have different carbohydrate structure if they are expressed in different cells. Although it has been recently demonstrated that some bacteria can attach the carbohydrate chains, typical bacteria, for example *E. coli*, are known not to do. Proteins expressed in *E. coli* do not contain the carbohydrate chains, and thus, *E. coli*-derived EPO, which does not contain the carbohydrate chains, exhibits positive in vitro activity but no in vivo activity. It is because deglycosylated EPO is rapidly eliminated from the human body and has extremely short half-life. In conclusion, the carbohydrate chains play a very important role in the activity of EPO.

Many studies have been made to enhance the activity of EPO. The main approach is substitutions of some amino acids of EPO by mutagenesis on the EPO gene. For example, PCT/US94/09257, filed by Amgen and titled "Erythropoietin analogs," discloses a method to increase in vivo half-life of EPO by increasing the carbohydrate contents through mutagenesis. Also, an attempt to increase in vivo half-life of EPO was made by formation of EPO dimer. See, A. J. Sytkowski et al., *J.B.C.* vol. 274, No. 35, pp24773–24778. Besides, another known method is to enhance in vivo activity of EPO by fusing new amino acids, peptides, or protein fragments with EPO molecule in the genetic engineering manner and increasing the carbohydrate content, i.e., sialic acid content of EPO. However, all amino acids, peptides, or heterogeneous protein fragments may not be used for this purpose. In most cases, such modifications may result in decrease or loss of inherent activity of protein and may cause a problem of antigenicity when used in vivo.

Although it is not related to EPO, fusion proteins or chimeric proteins have been studied, for example, for follicle stimulating hormone that is a kind of sex hormone. See, Furuhashi et al., 1995, *Mol. Endocrinol*. However, the methods have not been applied to the industry since protein modifications using a genetic engineering method have many risks. That is, in most cases, the target protein may not be readily obtained without professional skills, and on the contrary, the inherent activity of protein may be decreased or lost by the addition or substitution of new amino acids.

DISCLOSURE OF THE INVENTION

The present inventors have extensively studied new methods for enhancing in vivo activity of EPO by fusing new amino acids, peptides, or protein fragments with EPO molecule, and so increasing the carbohydrate content thereof. As a result, the present inventors have discovered that a fusion protein of EPO obtained by fusing a carboxy terminal peptide (CTP, below) of thrombopoietin (TPO, below), a protein that already exists in the human body, with the carboxy terminal of EPO has highly enhanced in vivo half-life due to a lot of amino acids that increase glycosylation site without loss of the inherent activity of EPO, and does not cause any antigenicity when applied to the human body. Then, the present inventors have completed the present invention.

Therefore, the object of the present invention is to provide a fusion protein having enhanced in vivo activity of human EPO and containing CTP of TPO fused with human EPO at the carboxy terminal thereof.

Another object of the present invention is to provide a nucleic acid encoding the fusion protein, a recombinant vector containing the nucleic acid, and a host cell line transformed with the recombinant vector.

Further object of the present invention is to provide a process for preparation of the fusion protein having enhanced in vivo activity of human EPO by cultivating the transformed cell line.

First, the present invention relates to a fusion protein having enhanced in vivo activity of human EPO and containing CTP of TPO fused with human EPO at the carboxy terminal thereof. The CTP preferably comprises the amino acid sequence of SEQ ID No. 1 that corresponds to amino acids of positions 176 to 353 (LTP, below) or parts thereof, particularly the amino acid sequence of SEQ ID No. 2 that corresponds to amino acids of positions 337 to 353 (STP, below).

Particularly, the fusion protein according to the present invention may comprise the amino acid sequence of SEQ ID No. 3 or 4.

Second, the present invention relates to a nucleic acid encoding the fusion protein, a recombinant vector containing the nucleic acid, and a host cell line, preferably CHO (Chinese hamster ovary) cell, transformed with the recombinant vector.

Third, the present invention relates to a process for preparation of the fusion protein having enhanced in vivo activity of human EPO by cultivating the transformed cell line.

Below, the present invention will be explained in more detail.

BRIEF DESCRIPTION OF THE DRAWINGS

FIGS. 1a and 1b show the nucleotides (SEQ ID NOS 15 & 16) and amino acid sequences (SEQ ID NOS 1 & 2) of carboxy terminal peptides (LTP, STP) of TPO;

FIGS. 2aa and 2ab show the nucleotide (SEQ ID NO: 17) and amino acid sequence (SEQ ID NO: 3) of ELTP that is a fusion protein of EPO and the peptide LTP, and FIG. 2b shows the nucleotide (SEQ ID NO: 18) and amino acid sequence (SEQ ID NO: 4) of ESTP that is a fusion protein of EPO and the peptide STP;

BEST MODE FOR CARRYING OUT THE INVENTION

The present invention comprises the steps of preparation and cloning of a gene of the desired fusion protein, construction of an expression vector containing the desired gene, transformation of an animal cell, expression, purification, and biological assay.

(1) Preparation of Gene

EPO cDNA may be obtained by performing the conventional PCR technique (PCR PreMix Kit of Bioneer Co.) using the complementary primers of EPO cDNA terminals (EP1 and EP2) from cDNA library of human-derived fetal liver (Invitrogen Co.). TPO cDNA may be obtained using the complementary primers of TPO cDNA terminals (T1 and T2) according to the same manner.

```
EP1:  ATGGGGGCACGAATGTCCTGCCTGGCTGG   (SEQ ID No.5)

EP2:  GTCCCCTGTCCTGCAGGCCT            (SEQ ID No.6)

T1:   ATGGATCTGACTGAATTGCTCCTC        (SEQ ID No.7)

T2:   TTACCCTTCCTGAGACAGATTCTGGGA     (SEQ ID No.8)
```

EPO cDNA and TPO cDNA obtained by PCR are cloned to pGEM-T (Promega Co.), a cloning vector, respectively. The pGEM-EPO and pGEM-TPO are then sequenced, and used as a template for the following procedures.

LTP, a CTP gene of TPO used in the present invention, may be obtained by performing PCR using pGEM-TPO as a template and primers EL1 and T2.

EL1: GAGGCCTGCAGGACAGGGGACGCCCCAC-CCACCACAGCTGTCC (SEQ ID No. 9)

The primer EL1 contains a gene extended to the position of restriction enzyme StuI, which is located near the 3' terminal of EPO, and a part of 5' terminal of LTP gene (amino acids of positions 176 to 353 of TPO) at the same time. On the other hand, PCR is performed using pGEM-EPO as a template and primers EP1 and EP2 to give EPO gene only. Thus obtained EPO and LTP genes are treated with restriction enzyme StuI, respectively. Then, fragments of EPO and LTP genes are ligated and the ligation product is used as a template in the PCR procedure using primers EP 11 and L2 to give a gene fragment ELTP having about 1113 bps.

```
EP11: TAAGCTTATGGGGGTGCACGAATGT    (SEQ ID No.10)

L2:   TGGATTCTTACCCTTCCTGAGACAGATTC (SEQ ID No.11)
```

Figure 3A:
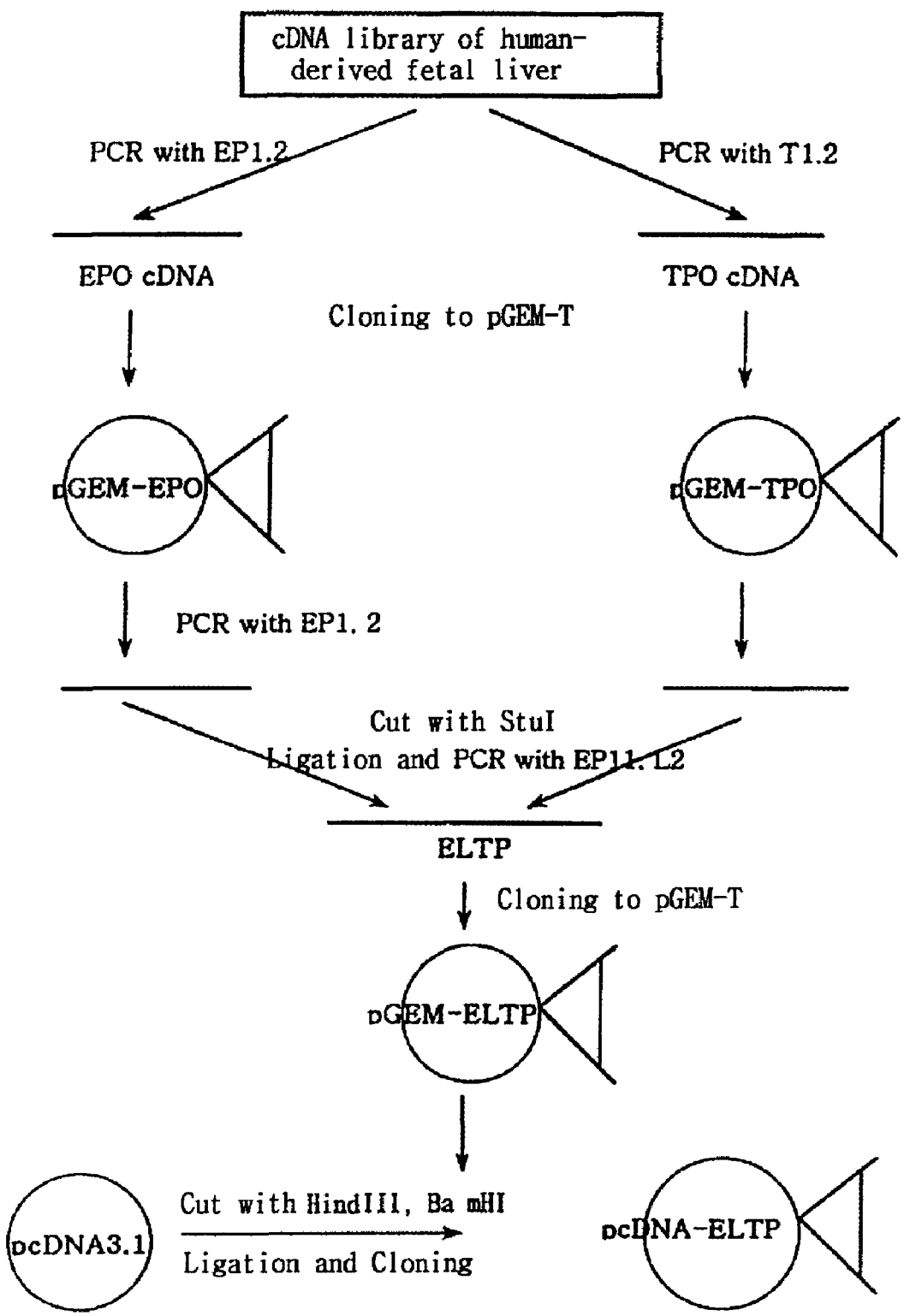
FIGS. 3a and 3b are schemes showing the procedures to prepare the expression vectors, pcDNA-ELTP and pcDNA-ESTP.

This gene is cloned to a cloning vector of pGEM-T and then sequenced (pGEM-ELTP, FIG. 3a).

Further, the STP gene used in the present invention may be obtained by synthesis and self-priming PCR procedure. Synthesized gene fragments are the following ES1, S2, S3 and the above L2.

```
ES1:
AGGGGAGGCCTGCAGGACAGGGGACCCTCTTCTAA  (SEQ ID No.12)

S2:
GTGGGTGTAGGATGTGTTTAGAAGAGG          (SEQ ID No.13)

S3:
TACACCCACTCCCAGAATCTGTCTC            (SEQ ID No.14)
```

1 µl (50 pmole/µl) of each 4 gene fragments is taken and PCR is performed using high fidelity Taq system of BM Co.

The gene fragment of about 50 bps (STP gene) is identified in 1% agarose gel. This gene encodes the 17 amino acids (amino acids of positions 337 to 353) of the carboxy terminal of TPO (FIG. 1).

PCR is performed using pGEM-EPO as a template and primers EP11 and EP2 to give EPO gene only. This EPO gene and the STP gene are used as templates at the same time and primers EP11 and L2 are used in a PCR using the high fidelity Taq system of BM Co. to give the desired fusion gene, ESTP gene, of about 630 bps. This gene is cloned to pGEM-T, a cloning vector, and then sequenced (pGEM-ESTP, FIG. 3b).

(2) Construction of Expression Vector pcDNA3.1 vector of Invitrogen Co. is used as an expression vector.

Figure 3B:
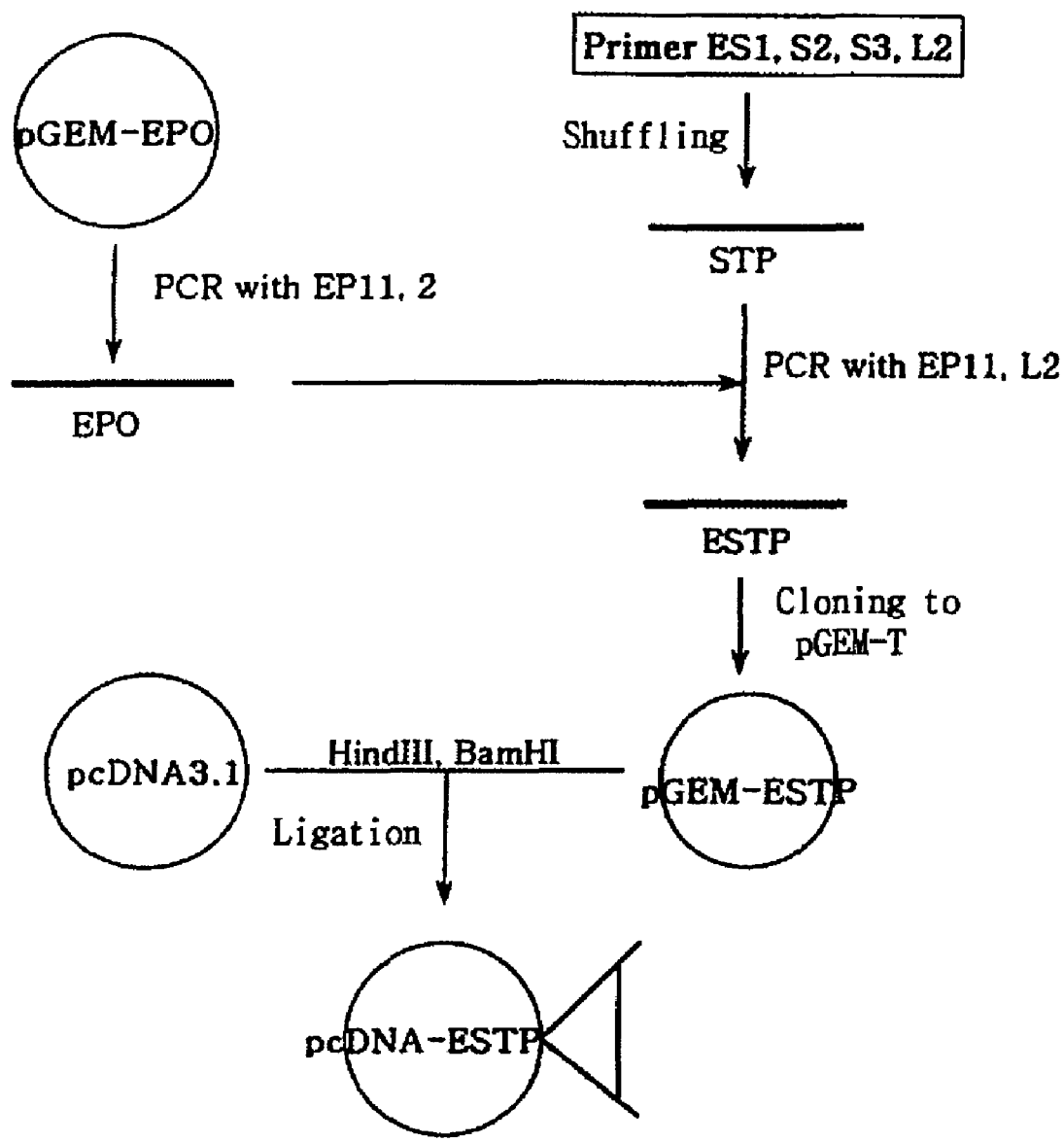

The pcDNA3.1 vector is treated with restriction enzymes HindIII and BamHI to make a linear vector, and PGEM-ELTP and pGEM-ESTP are also treated with the same restriction enzymes, HindIII and BamHI, respectively. The digested pcDNA3.1, ELTP, and ESTP genes are isolated using Qiagen extraction kit on agarose gel. After each ligation of the genes, the ligation product is introduced into E. coli NM522. Plasmids are isolated from the colonies that have been formed from cultivation of the transformed E. coli in LB-ampicillin plate overnight, and are treated with restriction enzymes, HindIII and BamHI. Colonies having ELTP or ESTP gene are then screened by 1% agarose gel electrophoresis. These plasmids are designated as pcDNA-ELTP and pcDNA-ESTP, respectively (FIGS. 3a and 3b).

(3) Transformation of CHO Cell and Expression

CHO cells (DG44) are cultivated to a confluency of 40~80% ($1~4 \times 10^5$ cells/60 mm dish) in a 60 mm cell culture dish. 3 µl of superfection reagent (BM Co.) and 97 µl of cell culture medium (α-MEM with media, no serum, no antibiotics) are mixed well, and pcDNA-ELTP (=0.1 µg/µl, about 2 µg) and vector pLTRdhfr26 (ATCC37295, 0.2 µg) having dhfr gene are added thereto. The mixture is reacted for 5~10 minutes at room temperature and then added to the cells as prepared above. After one day, the medium is refreshed with a medium containing G418 in an amount of 500 µg/ml (α-MEM without media, 10% FBS). The medium is then refreshed with the G418 medium containing 500 µg/ml of G418 for 7~10 days, during which cells without G418 resistance gene and negative control cells are completely killed. Selected cells on G418 medium are cultivated sufficiently and an expressed ELTP protein is identified using EPO ELISA kit of BM Co. The same process is applied to ESTP expression vector and then an expressed ESTP fusion protein is also identified in the same manner.

(4) Purification of the Expressed ELTP and ESTP

Affinity resin for isolation and purification is prepared using anti-EPO monoclonal antibody (R&D Co.) as follows:

0.3 g of CNBr-activated Sepharose 4B is swelled for 20 minutes in 1 mM HCl, and the resin is moved to a column and washed with 1 mM HCl. The resin is washed with 4 ml of coupling buffer (0.1M NaHCO$_3$, 0.5M NaCl, pH 8.3), immediately mixed with anti-EPO monoclonal antibody (500 μg/vial) contained in 4 ml of coupling buffer, and reacted for 2 hours at room temperature with stirring the tube. Refreshed with blocking buffer (0.2M glycine, pH 8.0), the resin is reacted at room temperature for 2 hours with stirring the tube. Then, the resin is washed with 6.5 ml of coupling buffer, 6.5 ml of acetate buffer (0.1M acetic acid, 0.5M NaCl, pH 4), and 6.5 ml of coupling buffer in the order. A column is prepared using such obtained resin and purification is conducted as described below.

Figure 4:
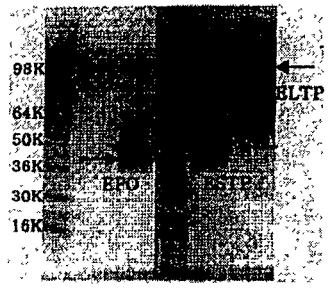
FIG. 4 is an electrophoresis photograph of expressed ELTP and ESTP.

Cells are cultivated in serum free medium for one day, and the medium is concentrated to about 5 folds using Centriprep (Millipore MWCO 10,000). This concentrate is loaded to a column equilibrated in advance with PBS at a flow rate of 20 ml/hr, and washed again with PBS. Elution buffer (0.1 M glycine, pH 2.8) is applied to the column and the eluent is immediately titrated with 1M Tris to pH 7.5. The purity is at least 97% when analyzed by SDS-PAGE and silver staining (FIG. 4).

(5) Activity Measurement by Bioassay Method

In the bioassay test using mouse spleen cells treated with phenylhydrazine, the ELTP and ESTP, which are expressed and properly purified, show higher activity than EPO. It demonstrates that the fused carboxy terminals in the ELTP and ESTP may not inhibit activity of EPO itself.

(6) Pharmacokinetic Experiments

Figure 5:
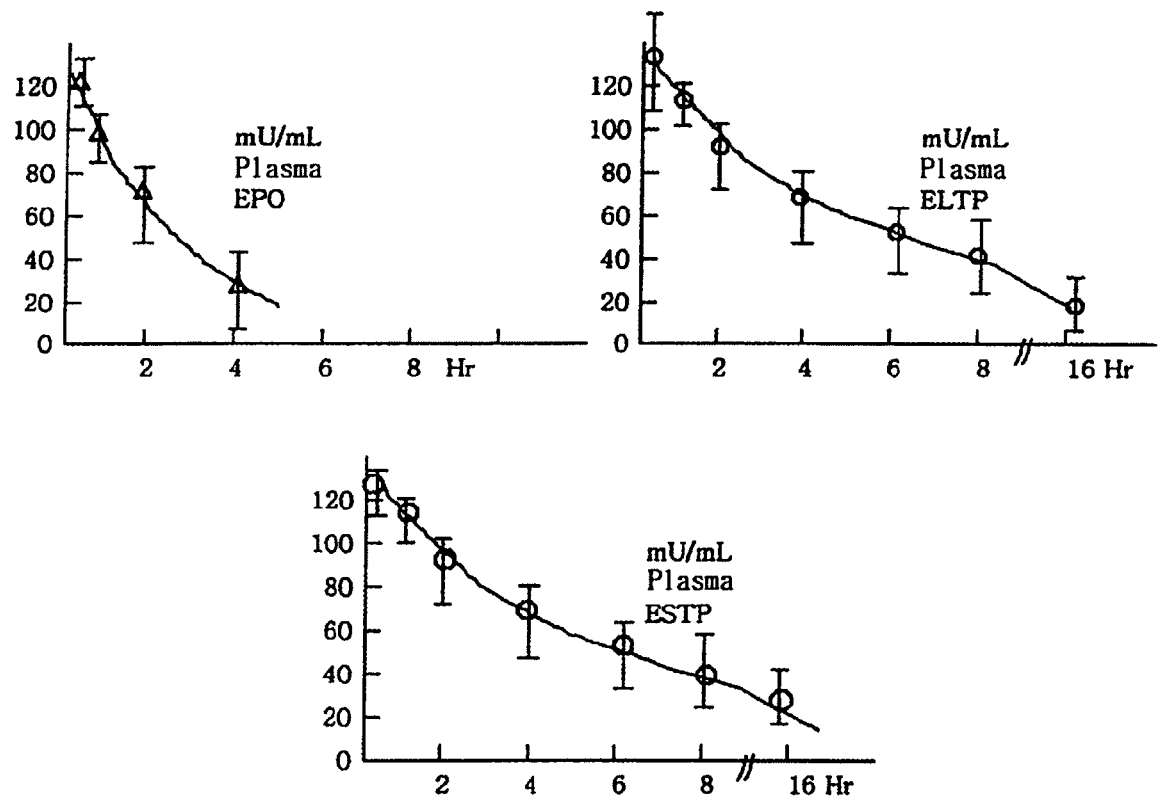
FIG. 5 is a graph showing the pharmacokinetic results of EPO, ELTP, and ESTP.

Pharmacokinetic experiments are performed to mice to determine whether the prepared ELTP and ESTP actually have prolonged in vivo half-life. The candidate substance is intravenously administered to 4 mice in an amount of 20 units/mouse. In order to identify the time-lapse concentration in blood, blood is taken from the mice at an interval of 30 minutes and concentrations are measured using EIA kit of Boehringer Mannheim Co. In the pharmacokinetic experiments to mice, the candidate substances, ELTP and ESTP, show far longer half-life than the control EPO (FIG. 5).

The present invention will be more specifically explained in the following examples. However, it should be understood that the following examples are intended to illustrate the present invention but not to limit the scope of the present invention in any manner.

EXAMPLE 1

Preparation of Gene

EPO cDNA was obtained by performing the conventional PCR (PCR PreMix Kit of Bioneer Co.) using the primers EP1 and EP2 that are complementary to the terminals of EPO cDNA, in an amount of 50 pmole, respectively, from cDNA library of human-derived fetal liver (Invitrogen Co.). TPO cDNA was obtained using the primers T1 and T2, complementary to the terminals of TPO cDNA, according to the same manner. Total 30 cycles of PCR were performed using high fidelity Taq system of BM Co. under the condition of 52° C. for 40 seconds for annealing, 72° C. for 55 seconds, and 94° C. for 20 seconds to give EPO cDNA and TPO cDNA. They were cloned to pGEM-T (Promega Co.), a cloning vector, respectively. That is, the PCR products were eluted from 1% agarose gel and ligated into pGEM-T, which was then introduced into E. coli NM522. The transformed E. coli was cultivated overnight in LB-ampicillin plate containing X-gal/IPTG. Plasmids were purified from the white colonies and treated with restriction enzymes, SacI and SacII, to screen the colonies containing the respective cDNAs. The vectors obtained at this stage were designated as pGEM-EPO and pGEM-TPO, which were then sequenced, and used as templates for the following procedures.

LTP, CTP gene of TPO used in the present invention, was obtained by performing total 30 cycles of PCR using the high fidelity Taq system of BM Co. and using pGEM-TPO as a template and primers, EL1 and T2 (50 pmole), under the condition of 50° C. for 40 seconds for annealing, 72° C. for 45 seconds, and 94° C. for 20 seconds. The primer EL1 contains a gene from the position of restriction enzyme StuI, which is located near the 3' terminal of EPO, to the 3' terminal, and a part of 5' terminal of LTP gene at the same time. A gene fragment of about 534 bps was identified on 1% agarose gel (LTP gene). This gene encodes the 178 amino acids of the carboxy terminal of TPO (amino acids of positions 176 to 353) (FIG. 1).

On the other hand, PCR was performed using pGEM-EPO as a template and primers EP1 and EP2 to give EPO gene only.

Thus obtained EPO and LTP genes were treated with restriction enzyme StuI, respectively. Then, fragments of EPO and LTP genes were purified by Qiagen extraction kit and ligated with a ligase. The ligation product of EPO and LTP genes was used as a template in total 30 cycles of PCR procedure using primers EP11 and L2 (50 pmole) and using the high fidelity Taq system of BM Co. under the condition of 55° C. for 40 seconds for annealing, 72° C. for 60 seconds, and 94° C. for 20 seconds to give the desired fusion gene of ELTP having about 1113 bps. This gene was cloned to a cloning vector of pGEM-T in the same manner as above and then sequenced (pGEM-ELTP, FIG. 3a).

STP gene was obtained by synthesis and self-priming PCR procedure. Synthesized DNA fragments were ES1, S2, S3 and L2. 1 μl (50 pmole/μl) of each of the 4 DNA fragments was taken and total 15 cycles of PCR were performed using the high fidelity Taq system of BM Co. under the condition of 55° C. for 40 seconds for annealing, 72° C. for 40 seconds, and 94° C. for 20 seconds. A gene fragment of about 50 bps was identified on 1% agarose gel (STP gene). This gene encodes the 17 amino acids of the carboxy terminal of TPO (amino acids of positions 337 to 353) (FIG. 1).

PCR was performed using pGEM-EPO as a template and primers EP11 and EP2 in the same manner as above to give EPO gene only. This EPO gene and the STP gene were used as templates at the same time and primers of EP11 and L2 were used in total 30 cycles of PCR using high fidelity Taq system of BM Co. under the condition of 58° C. for 40 seconds for annealing, 72° C. for 50 seconds, and 94° C. for 20 seconds to give the desired fusion gene, ESTP gene, of about 630 bps. This gene was cloned to pGEM-T, a cloning vector, and then sequenced (pGEM-ESTP, FIG. 3b).

EXAMPLE 2

Construction of Expression Vectors pcDNA-ELTP and pcDNA-ESTP pcDNA3.1 vector of Invitrogen Co. was used as an expression vector. ELTP and ESTP genes that are cloned to pGEM-T vector contain HindIII and BamHI recognition sites at terminals, respectively. pcDNA3.1, pGEM-ELTP and pGEM-ESTP were treated with restriction enzymes, HindIII and BamHI, respectively. The linearized pcDNA3.1, ELTP, and ESTP genes were isolated using Qiagen extraction kit on agarose gel. After ligation of pcDNA3.1 with ELTP or ESTP, the ligation product was introduced into *E. coli* NM522. Plasmids were isolated from the colonies that had been formed from cultivation of the transformed *E. coli* in LB-ampicillin plate overnight, and were treated with restriction enzymes, HindIII and BamHI. Colonies having ELTP or ESTP gene were then screened by 1% agarose gel electrophoresis. These plasmids were designated as pcDNA-ELTP and pcDNA-ESTP, respectively (FIG. 3).

EXAMPLE 3

Transformation of CHO Cell and Expression

CHO cells (DG44) were cultivated to a confluency of 40~80% (1~4×10$^5$ cells/60 mm dish) in a 60 mm cell culture dish. 3 µl of superfection reagent (BM Co.) and 97 µl of cell culture medium (α-MEM with media, no serum, no antibiotics) were mixed well, and plasmid pcDNA-ELTP (=0.1 µg/µl, about 2 µg) and vector pLTRdhfr26 (ATCC37295, 0.2 µg) having dhfr gene were added thereto. The mixture was reacted for 5~10 minutes at room temperature and then added to the cells as prepared above. After one day, the medium was refreshed with a medium containing G418 in an amount of 500 µg/ml (α-MEM without media, 10% FBS). The medium was then refreshed with the G418 medium containing 500 µg/ml of G418 for 7~10 days, during which cells without G418 resistance gene and negative control cells were completely killed. Selected cells on G418 medium were cultivated sufficiently and an expressed ELTP protein was identified using EPO ELISA kit of BM Co. The same process was applied to pcDNA-ESTP.

EXAMPLE 4

Purification of the Expressed Fusion Proteins

Affinity resin for isolation and purification was prepared using anti-EPO monoclonal antibody (R&D Systems Co.) as follows:

0.3 g of CNBr-activated Sepharose 4B was swelled for 20 minutes in 1 mM HCl, and the resin was moved to a column and washed with 1 mM HCl. The resin was washed with 4 ml of coupling buffer (0.1M NaHCO$_3$, 0.5M NaCl, pH 8.3), immediately mixed with anti-EPO monoclonal antibody (500 µg/vial) contained in 4 ml of coupling buffer in a tube, and reacted for 2 hours at room temperature with stirring the tube. Refreshed with blocking buffer (0.2M glycine, pH 8.0), the resin was reacted at room temperature for 2 hours with stirring the tube. Then, the resin was washed with 6.5 ml of coupling buffer, 6.5 ml of acetate buffer (0.1M acetic acid, 0.5M NaCl, pH 4), and 6.5 ml of coupling buffer in the order. A column was prepared using such obtained resin and purification was conducted as described below.

Cells were cultivated in serum free medium for one day, and the medium was concentrated to about 5 folds using Centriprep (Millipore, MWCO 10,000). This concentrate was loaded to a column equilibrated in advance with PBS at a flow rate of 20 ml/hr, and washed again with PBS. Elution buffer (0.1M glycine, pH 2.8) was applied to the column and the eluent was immediately titrated with 1M Tris to pH 7.5. SDS-PAGE results of the purified ELTP and ESTP are shown in FIG. 4. The purity was at least 97% when analyzed by SDS-PAGE and silver staining.

EXAMPLE 5

Activity Measurement by Bioassay Method

Phenylhydrazine was injected to a mouse once a day for 2 days at a dose of 60 mg/kg. After 3 days, enlarged spleen was separated and ground with a homogenizer to obtain spleen cells. The spleen cells were diluted to 6×10$^6$ cells/ml and 100 µl of the cell solution was introduced into each well of a 96 well plate. 0~500 mU/ml of authentic EPO and 100 mU/ml of the expressed fusion protein were added to each well, and the plate was allowed to stand at 37° C. for 22 hours in a CO$_2$ incubator. 50 µl of dimethyl $^3$[H]-thymidine (20 µCi/ml) was added to each well, further reacted for 2 hours in the same incubator, and the reaction solution was then adsorbed onto a glass filter (Nunc 1–73164) per each well. The filters were washed with physiological saline 3 times and the amount of radioactivity of each filter was measured using β counter. The activities of the fusion proteins, ELTP and ESTP were shown to be comparable to or higher than that of authentic EPO, which demonstrated that the carboxy terminals fused into EPO did not inhibit activity of EPO itself.

EXAMPLE 6

Pharmacokinetic Experiments

Pharmacokinetic experiments were performed to mice to determine whether the prepared candidate substance actually has prolonged in vivo half-life. The fusion protein purified according to the process of Example 5 was intravenously administered to 4 mice in an amount of 20 units/mouse. In order to identify the time-lapse concentration in blood, blood was taken from the mice at an interval of 30 minutes and concentrations were measured using EIA kit of Boehringer Mannheim Co. The results are shown in FIG. 5. As can be seen from FIG. 5, ELTP and ESTP show about three times longer half-life than the control, EPO, respectively (half-life of EPO was 22 minutes, that of ELTP was 60 minutes, and that of ESTP was 57 minutes).

INDUSTRIAL APPLICABILITY

The fusion proteins according to the present invention have highly increased in vivo half-life of EPO due to the presence of amino acids that increase the carbohydrate chains without influencing the inherent activity of EPO. Further, the fusion proteins do not cause any problem of antigenicity when applied to the human body since the fused peptide, LTP or STP, is a peptide that already exists in the body.

The invention claimed is:

1. A fusion protein wherein a carboxy terminal peptide (CTP) of thrombopoietin (TPO) consisting of the amino acid sequence of SEQ ID NO. 2 is fused with human erythropoietin (EPO) at the carboxy terminal of the human EPO.

2. A nucleic acid encoding the fusion protein according to claim 1.

3. A process for preparation of a fusion protein having enhanced in vivo activity of human EPO-compared to wild type human EPO comprising cultivation of a host cell line transformed with a recombinant vector containing the nucleic acid according to claim 2.

* * * * *